United States Patent [19]

Bruchmann et al.

[11] Patent Number: 6,022,938
[45] Date of Patent: Feb. 8, 2000

[54] COMPOUNDS WITH ISOCYANATE GROUPS AND MASKED GROUPS REACTIVE IN RELATION TO ISOCYANATES

[75] Inventors: Bernd Bruchmann, Freinsheim; Hans Renz, Meckenheim; Günter Mohrhardt, Speyer, all of Germany

[73] Assignee: Basf Aktiengesellschaft, Ludwigshafen, Germany

[21] Appl. No.: 09/091,239

[22] PCT Filed: Dec. 16, 1996

[86] PCT No.: PCT/EP96/05634

§ 371 Date: Jun. 18, 1998

§ 102(e) Date: Jun. 18, 1998

[87] PCT Pub. No.: WO97/23536

PCT Pub. Date: Jul. 3, 1997

[30] Foreign Application Priority Data

Dec. 21, 1995 [DE] Germany .............. 195 47 974

[51] Int. Cl.[7] .................................. C08G 18/28
[52] U.S. Cl. .............. 528/73; 252/182.2; 252/182.21; 252/182.22; 540/544; 540/553; 540/609; 544/63; 544/335; 549/10; 549/11; 549/22; 549/30; 549/39; 549/76; 549/77; 549/78; 549/79; 549/373; 549/375; 549/493; 549/510
[58] Field of Search ............ 528/73; 252/182.2, 252/182.21, 182.22; 540/544, 553, 609; 544/63, 335; 549/10, 11, 22, 30, 39, 76, 77, 78, 79, 373, 375, 493, 510

[56] References Cited

U.S. PATENT DOCUMENTS 4,002,601  1/1977  Hajels ........................ 540/544

FOREIGN PATENT DOCUMENTS 585835    3/1994   European Pat. Off. .
682012   11/1995   European Pat. Off. .
19524046  1/1997   European Pat. Off. .

Primary Examiner—Rachel Gorr
Attorney, Agent, or Firm—Oblon, Spivak, McClelland, Maier & Neustadt, P.C.

[57] ABSTRACT

Isocyanato compounds with capped, isocyanate-reactive groups are those of the formula I

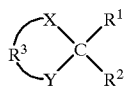

I where
$R^1$ and $R^2$ are hydrogen, $C_1$–$C_{10}$-alkyl, $C_6$–$C_{10}$-aryl or $C_7$–$C_{10}$-aralkyl or together form $C_3$–$C_{10}$-alkanediyl, X and Y are —O—, —S— or

—NR$^4$, where $R^4$ is hydrogen, $C_1$–$C_{20}$-alkyl which is uninterrupted or interrupted by oxygen atoms in ether function, or is $C_6$–$C_{10}$-aryl or $C_7$–$C_{10}$-aralkyl,
$R^3$ is $C_1$–$C_{10}$-alkanediyl which together with —X—CR$^1$R$^2$—Y— forms a 4–7-membered ring,
in which either one hydrogen in $R^3$ or the radical $R^4$ in

—NR$^4$ is replaced by
an allophanate group $R^{Ia}$

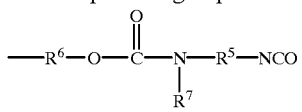

in which
$R^5$ is a divalent aliphatic, alicyclic, araliphatic or aromatic $C_2$–$C_{20}$ hydrocarbon unit,
$R^6$ is a single bond or a divalent aliphatic, alicyclic, araliphatic or aromatic $C_1$–$C_{20}$ hydrocarbon unit or a mono- or poly($C_2$–$C_4$-alkylene oxide) unit, and
$R^7$ is a carbamoyl radical

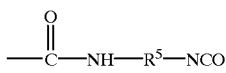

or a biuret group $R^{Ib}$

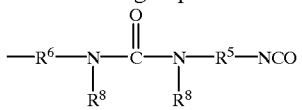

in which one $R^8$ is hydrogen and the other is as defined for $R^7$
or a biuret group $R^{Ic}$

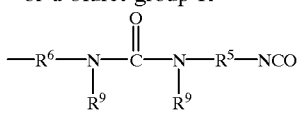

in which one $R^9$ is as defined for $R^7$ and the other is as defined for $R^1$
or a thioallophanate group $R^{Id}$

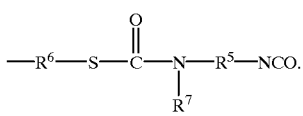

11 Claims, No Drawings

COMPOUNDS WITH ISOCYANATE GROUPS AND MASKED GROUPS REACTIVE IN RELATION TO ISOCYANATES

The invention relates to isocyanato compounds (compounds containing isocyanate groups) with capped, isocyanate-reactive groups, of the general formula I

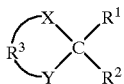
                              I where
- $R^1$ and $R^2$ are hydrogen, $C_1$–$C_{10}$-alkyl, $C_6$–$C_{10}$-aryl or $C_7$–$C_{10}$-aralkyl or together form $C_3$–$C_{10}$-alkanediyl,
- X and Y are —O—, —S— or

where $R^4$ is hydrogen, $C_1$–$C_{20}$-alkyl which is uninterrupted or interrupted by oxygen atoms in ether function, or is $C_6$–$C_{10}$-aryl or $C_7$–$C_{10}$-aralkyl, $R^3$ is $C_1$–$C_{10}$-alkanediyl which together with —X—$CR^1R^2$—Y— forms a 4–7-membered ring, in which either one hydrogen in $R^3$ or the radical $R^4$ in

is replaced by
an allophanate group $R^{Ia}$

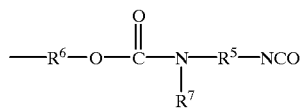

in which
- $R^5$ is a divalent aliphatic, alicyclic, araliphatic or aromatic $C_2$–$C_{20}$ hydrocarbon unit,
- $R^6$ is a single bond or a divalent aliphatic, alicyclic, araliphatic or aromatic $C_1$–$C_{20}$ hydrocarbon unit or a mono- or poly($C_2$–$C_4$-alkylene oxide) unit, and
- $R^7$ is a carbamoyl radical

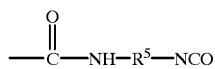

or a biuret group $R^{Ib}$

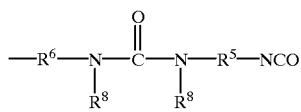

in which one $R^8$ is hydrogen and the other is as defined for $R^7$ or a biuret group $R^{Ic}$

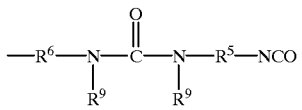

in which one $R^9$ is as defined for $R^7$ and the other is as defined for $R^1$ or a thioallophanate group $R^{Id}$

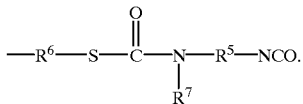

The invention additionally relates to crosslinking polyurethane coating compositions comprising compounds of the formula I and to coating methods in which these crosslinking polyurethane coating compositions are used.

Crosslinking polyurethane coating compositions are generally known, for example in the form of 2-component materials (cf. Kunststoff Handbuch, Volume 7, Polyurethane, 2nd Edition, 1983, Carl Hanser Verlag Munich, Vienna, pp. 540–561). These two-component systems contain a polyol as binder and a compound having two or more free isocyanate groups as crosslinking component.

Since a high molecular weight network develops after the two components are mixed, they can only be mixed directly prior to application to the workpiece to be coated. For the processer of such systems this means that the individual coating steps must follow on smoothly from one another in terms of time, since following the mixing of the components a defined quantity of coating material must be processed within a certain time.

This complication in the processing of these systems is accepted by the processer, since the resulting coatings are markedly superior to those obtained from the generally known, noncrosslinking one-component systems, which can in principle be stored for as long as is desired.

This superiority relates in particular to service properties such as
- lack of sensitivity to mechanical stresses such as tension, extension, impact or abrasion
- resistance to moisture (for example in the form of steam) and dilute chemicals
- resistance to environmental effects such as temperature fluctuations and UV radiation
- high gloss of the coated surfaces.

In order for coating materials to be able to be applied without problems by conventional techniques, for example by spray application to the surface to be coated, they should be of limited viscosity. Consequently, coating materials based on two-component systems usually include solvents. However, the solvent content of these materials causes problems, since the coatings processer has to take technically complex measures in order to avoid the passage into the atmosphere of the solvents released during application and drying of the coating materials. Consequently, many attempts have been made to find a way out of this situation of conflicting aims and to provide two-component systems which are not only of low viscosity coupled with high solids content but which also have a high profile in terms of the abovementioned service properties.

EP-A-0 585 835 describes two-component systems where the isocyanate component comprises trimerized diisocyanates containing isocyanurate groups, where some of the remaining isocyanate groups are reacted with a monohydric alcohol to form urethane groups.

Polyisocyanates containing isocyanurate groups and allophanate groups, and formed from a diisocyanate and a polyester monoalcohol, are described in DE-A-O 15 155. These polyisocyanates can be used as hardeners in two-component polyurethane coatings.

Additionally, in order to reduce the viscosity of the two-component systems, reactive diluents have been developed. These compounds have a similar effect on the viscosity of two-component systems to that of a solvent. Unlike solvents, however, during the drying or hardening of the two-component systems employed as coating material the reactive diluents react with the other binder components to form a high molecular weight network.

The German Patent Application with the file reference P 19524046.4 describes a reactive diluent which is a compound containing one isocyanate, one urethane and one thiourethane or urea group and 2 capped, isocyanate-reactive groups. However, these compounds contain neither an allophanate group nor a biuret group.

Despite the fact that it has already been possible with the previously known two-component systems to make some progress regarding the reduction in the solvent content, there continues to be a need for improvement in this respect.

It is therefore an object of the present invention to provide two-component systems, which couple high solids content with low viscosity and can be processed to give coatings with a good profile of properties, and components for such systems. It was also an object to provide crosslinking one-component systems, which couple high solids content with low viscosity, are stable on storage and can be processed to give coatings whose quality is at least equal to those obtained from two-component systems, and components for these one-component systems.

We have found that these objects are achieved by the isocyanato compounds (I) defined at the outset which contain capped, isocyanate-reactive groups, and by crosslinking one-component and two-component polyurethane coating compositions comprising these compounds (I).

Among the novel compounds of the formula I preference is given to those in which:

$R^1$ and $R^2$ are in particular hydrogen or $C_1$–$C_6$-alkyl, especially methyl, ethyl or isopropyl. Among the $C_3$–$C_{10}$-alkanediyl groups which $R^1$ and $R^2$ can form together, cyclopentyl and cyclohexyl are preferred.

Preferred radicals $R^4$ in the group $$-\underset{|}{\text{N}}R^4,$$

which can be X and/or Y, are $C_1$–$C_6$-alkyl, for example methyl, ethyl, n-propyl or n-butyl.

Particularly suitable groups $R^3$ are $C_2$–$C_{10}$-alkanediyls which, together with —X—$CR^1R^2$—Y—, form a 5- or 6-membered ring.

In the compounds of the formula I it is necessary for either a hydrogen of $R^3$, or $R^4$, to be substituted by an allophanate group $R^{Ia}$, a biuret group $R^{Ib}$, a biuret group $R^{Ic}$ or a thioallophanate group $R^{Id}$. The compounds of the formula I therefore carry a single group selected from the range of groups $R^{Ia}$, $R^{Ib}$, $R^{Ic}$ and $R^{Id}$. The group which can be $R^{Ia}$, $R^{Ib}$, $R^{Ic}$ or $R^{Id}$ is referred to below as $R^I$.

Particular preference is given to dioxolanes of the formula I.1

$$\text{I.1}$$

dioxanes of the formula I.2

$$\text{I.2}$$

in which $R^a$ is hydrogen or $C_1$–$C_{10}$-alkyl, or oxazolidine derivatives of the formula I.3

$$\text{I.3}$$

The units $R^5$ which are part of $R^I$ are preferably units derived from customary diisocyanates (cf. Kunststoff Handbuch, Volume 7, Polyurethane, 2nd Edition, 1983, Carl Hanser Verlag Munich, Vienna, Chapter 2.2.1) by abstraction of the two isocyanate groups.

Examples of customary diisocyanates are aliphatic diisocyanates such as tetramethylene diisocyanate, hexamethylene diisocyanate(1,6-diisocyanatohexane), octamethylene diisocyanate, decamethylene diisocyanate, dodecamethylene diisocyanate, tetradecamethylene diisocyanate, derivatives of lysine diisocyanate, tetramethylxylylene diisocyanate, trimethylhexane diisocyanate or tetramethylhexane diisocyanate, cycloaliphatic diisocyanates such as 1,4-, 1,3- or 1,2-diisocyanatocyclohexane, 4,4'-di(isocyanatocyclohexyl)methane, 1-isocyanato-3,3,5-trimethyl-5-(isocyanatomethyl)cyclohexane-(isophorone diisocyanate) or 2,4- or 2,6-diisocyanato-1-methylcyclohexane, and aromatic diisocyanates, such as 2,4- or 2,6-tolylene diisocyanate, p-xylylene diisocyanate, 2,4'- or 4,4'-diisocyanatodiphenylmethane, 1,3- or 1,4-phenylene diisocyanate, 1-chloro-2,4-phenylene diisocyanate, 1,5-naphthylene diisocyanate, diphenylene 4,4'-diisocyanate, 4,4'-diisocyanato-3,3'-dimethylbiphenyl, 3-methyldiphenylmethane 4,4'-diisocyanate, or diphenyl ether 4,4'-diisocyanate. Mixtures of these diisocyanates can also be present. Preference is given to hexamethylene diisocyanate and isophorone diisocyanate, and to 2,4- and 2,6-tolylene diisocyanate and 2,4'- and 4,4'-diphenylmethane diisocyanate.

$R^6$ preferably comprises branched and unbranched $C_1$–$C_4$-alkanediyl, especially methylene or ethylene. Other suitable units $R^6$ are mono- or poly($C_2$–$C_4$-alkylene oxide) units of the formula $$-\text{"alkylene"}-\left(\text{O}-\text{CH}_2-\underset{\underset{R^b}{|}}{\text{CH}}\right)_n-$$

in which alkylene is branched or unbranched $C_1$–$C_4$-alkanediyl, n is 1–20 and $R^b$ independently at each occurrence is methyl, ethyl or hydrogen.

In this context, both homopolymeric and copolymeric units derived from ethylene oxide, propylene oxide or butylene oxide are suitable.

The novel compounds of the formula I are employed as the B component in two-component polyurethane coating compositions, commonly in the form of mixtures (B) comprising a) compounds of the general formula I, b) customary isocyanates having on average at least 2 isocyanate groups (compounds II), c) compounds of the formula III

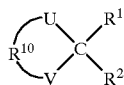

III where
$R^1$ and $R^2$ are as defined for formula I,
U and V are —O—, —S— or

where $R^{11}$ is hydrogen, $C_1$–$C_{10}$-alkyl which is uninterrupted or interrupted by oxygen atoms in ether function, or is $C_6$–$C_{10}$-aryl or $C_7$–$C_{10}$-aralkyl, and $R^{10}$ is $C_1$–$C_{10}$-alkanediyl which together with —U—$CR^1R^2$—V— forms a 4–7-membered ring, in which either one hdyrogen of $R^{10}$ or the radical $R^{11}$ in

is substituted by a urethane group $R^{IIIa}$

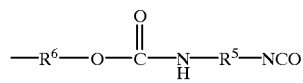

or a urea group $R^{IIIb}$

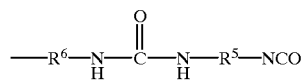

or a urea group $R^{IIIc}$

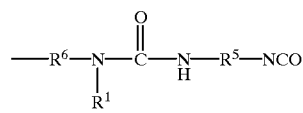

or a thiourethane group $R^{IIId}$

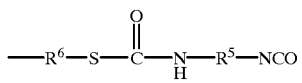

in which $R^5$ and $R^6$ are as defined for formula I.

Examples of suitable, customary isocyanates having on average at least 2 isocyanate groups (compounds II) are triisocyanates such as 2,4,6-triisocyanatotoluene, triphenylmethane triisocyanate or 2,4,4'-triisocyanatodiphenyl ether, or the mixtures of di-, tri- and higher polyisocyanates which are obtained by phosgenization of corresponding aniline/formaldehyde condensation products and constitute polyphenyl polyisocyanates containing methylene bridges.

Compounds II of particular interest are customary polyfunctional aliphatic polyisocyanates of the following groups:

(a) polyisocyanates which contain isocyanurate groups and are derived from aliphatic, cycloaliphatic, aromatic and/or araliphatic diisocyanates. Particularly preferred in this context are the corresponding isocyanato-isocyanurates based on hexamethylene diisocyanate and isophorone diisocyanate. The present isocyanurates are, in particular, simple trisisocyanatoalkyl or trisisocyanatocycloalkyl isocyanurates, which constitute cyclic trimers of the diisocyanates, or are mixtures with their higher homologs containing more than one isocyanurate ring. The isocyanato-isocyanurates generally have an NCO content of from 10 to 30% by weight, in particular from 15 to 25% by weight, and a mean NCO functionality of from 2.6 to 4.5.

Particularly suitable compounds II are isocyanurates of the general formula (IIa)

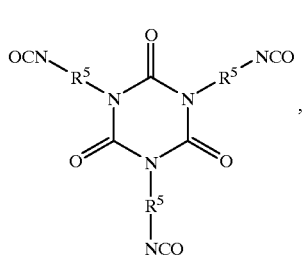

IIa or the oligomeric forms derived therefrom, in which $R^5$ is as defined for the compounds of formula I.

(b) Diisocyanates containing uretdione groups and having isocyanate groups attached to aromatic, aliphatic and/or cycloaliphatic structures, preferably derived from hexamethylene diisocyanate or isophorone diisocyanate. In the case of polyuretdione diisocyanates, these are dimerization products of diisocyanates.

(c) Polyisocyanates containing biuret groups and having isocyanate groups attached to aliphatic structures, especially tris(6-isocyanatohexyl)biuret or mixtures thereof with its higher homologs. These polyisocyanates containing biuret groups generally have an NCO content of from 10 to 30% by weight, in particular from 18 to 25% by weight, and a mean NCO functionality of from 2.8 to 4.5.

(d) Polyisocyanates containing urethane groups and/or allophanate groups and having isocyanate groups attached to aliphatic or cycloaliphatic structures, as can be obtained, for example, by reacting excess quantities of hexamethylene diisocyanate or isophorone diisocyanate with polyhydric alcohols such as trimethylolpropane, glycerol, 1,2-dihydroxypropane or mixtures thereof. These polyisocyanates containing urethane groups and/or allophanate groups generally have an NCO content of from 12 to 25% by weight and a mean NCO functionality of from 2.5 to 4.5.

(e) Polyisocyanates which contain oxadiazinetrione groups and are preferably derived from hexamethylene diisocyanate or isophorone diisocyanate. Polyisocyanates of this kind, containing oxadiazinetrione groups, can be prepared from diisocyanate and carbon dioxide.

(f) Carbodiimide- or uretonimine-modified polyisocyanates.

It is also possible for some of the isocyanate groups in the abovementioned polyisocyanates (a) to (f) to be reacted with monoalcohols.

Particularly suitable compounds of the formula III are known, for example, from the German Patent Application with the file reference P. 195 24 046.4.

Preferred units $R^1$, $R^2$, $R^5$ and $R^6$ in the compounds of the formula III are the same as those for the corresponding units of the formula I. In general, units $R^{10}$, $R^{11}$, U and V in formula III differ from the corresponding units $R^3$, $R^4$, X and Y in formula I only in that they may carry the group $R^{IIIa}$ instead of the group $R^{Ia}$, the group $R^{IIIb}$ instead of the group $R^{Ib}$, the group $R^{IIIc}$ instead of the group $R^{Ic}$ and the group $R^{IIId}$ instead of the group $R^{Id}$.

The compounds of the formula I are prepared with particular simplicity by reacting compounds of the formula IV

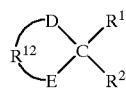    IV where $R^1$ and $R^2$ are as defined for formula I,
D and E are —O—, S or

where $R^{13}$ is hydrogen, $C_1$–$C_{10}$-alkyl which is uninterrupted or interrupted by oxygen atoms in ether function, or is $C_6$–$C_{10}$-aryl or $C_7$–$C_{10}$-aralkyl, and $R^{12}$ is $C_1$–$C_{10}$-alkanediyl which together with D-CR$^1$R$^2$-E forms a 4–7-membered ring, in which either one hydrogen in $R^{12}$ or the radical $R^{13}$ in

is substituted by
a radical $R^{IVa}$

—$R^6$—OH, a radical $R^{IVb}$

—$R^6$—NH$_2$, or a radical $R^{IVc}$

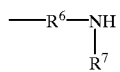

or a radical $R^{IVd}$

with a compound of the formula V

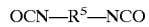    V at from 20 to 140° C. with a molar ratio of the compound of formula IV to the compound of formula V of from 1:1.5 to 1:20.

The reaction is generally performed without solvent or in solution and preferably under atmospheric pressure.

By choosing the starting compound IV with the appropriate substituents $R^{IVa}$, $R^{IVb}$, $R^{IVc}$ or $R^{IVd}$ it is possible to prepare specific novel compounds of the formula I and compounds of the formula III. The units D, E and $R^{12}$ in the starting compounds (compounds IV) differ from the corresponding units U, V and $R^{10}$ (compounds III) and X, Y and $R^3$ (compounds I) in the target compounds only, generally speaking, in that they carry different substituents $R^{IVa}$, $R^{IVb}$, $R^{IVc}$ and $R^{IVd}$ (compounds IV), $R^{IIIa}$, $R^{IIIb}$, $R^{IIIc}$ and $R^{IIId}$ (compounds III) and, respectively, $R^{Ia}$, $R^{Ib}$, $R^{Ic}$ and $R^{Id}$ (compounds I). The lower case letters a, b, c or d in the designations for the starting compounds and target compounds and in their characteristic radicals are allocated such that they are equal in the starting compounds and in the target compounds which can be prepared therefrom (in other words, for example, a compound with the substituent $R^{IVa}$ leads to Ia, with $R^1$, $R^2$, $R^5$ and $R^7$ being identical in both the starting and the target compound). Owing to their ease of preparation, particular preference is given to mixtures of compounds I, II and, if appropriate, III which are formed in the reaction of the corresponding starting compounds IV and V.

The reaction is usually ended when the starting compound of the formula IV in the reaction mixture has been consumed almost quantitatively by reaction.

Other reaction parameters are familiar to the person skilled in the art and can be chosen, for example, as described in EP-A-0 585 835, 0 496 208, 0 69 866, in U.S. Pat. Nos. 5,124,427, 5,258,482 and 5,290,902 and also DE-A-40 15 155 for the preparation of other biurets, allophanates and isocyanurates.

The reaction of the compounds IV and V is usually carried out in the presence of a catalyst in preferred quantities of from 10 to 5000 ppm by weight, based on the quantity of the compounds V employed.

Suitable catalysts are those which are generally known for the trimerization reaction of isocyanate groups, ie. for example the quaternary ammonium hydroxides described in EP-A-0 649 866, eg. N,N,N-trimethyl-N-(2-hydroxypropyl) ammonium hydroxide, or the quaternary ammonium carboxylates known from EP-A-0 182 203, eg. N,N,N-trimethyl-N-(2-hydroxypropyl)ammonium 2-ethylhexanoate, or organozinc compounds which are known as catalysts for allophanate formation, examples being zinc acetylacetonate or zinc 2-ethylcaproate.

The progress of the reaction is advantageously monitored by gel permeation chroamtography (GPC) or by determining the NCO content of the reaction mixture.

The reaction is usually ended when almost all of the starting compound IV has been converted, ie. can no longer be detected by GPC.

The reaction is conventionally ended by adding deactivators. Examples of suitable deactivators are inorganic or organic acids, the corresponding halides, and alkylating agents. Specific examples are phosphoric acid, monochloroacetic acid, dodecylbenzenesulfonic acid, benzoyl chloride and dimethyl sulfate, and preferably dibutyl phosphate and di-2-ethylhexyl phosphate. The deactivating agents can be employed in quantities of from 1 to 200 mol %, preferably from 20 to 100 mol %, relative to the catalyst.

After ending the reaction, any unreacted compound of the formula V is expediently separated off from the reaction mixture, preferably down to a content of less than 1.0% by weight, particularly preferably less than 0.5% by weight. If the compounds of the formula I are to be separated from those of the formula III, this can be done by gel permeation chromatography. However, separation is unnecessary in the majority of cases, since both compounds can be employed in two-component polyurethane coating compositions for similar purposes. The resulting product presents no handling problems and can generally be processed without special safety precautions.

The novel compounds of the formula I, alone or mixed with the compounds II and III, are employed as the B component in two-component polyurethane coating compositions whose A component generally comprises a hydroxy-functional polymer (A) devoid of isocyanate groups.

The hydroxy-functional polymers (A) are, for example, polymers with a hydroxyl content of from 0.1 to 20% by weight, preferably from 0.5 to 10% by weight. The number-average molecular weight $M_n$ of the polymers is preferably from 1000 to 100,000, particularly preferably from 2000 to 10,000. Preferred polymers are those of whose weight more than 50% is accounted for by $C_1$–$C_{20}$-alkyl (meth)acrylate, aromatic vinyl compounds having up to 20 carbon atoms, vinyl esters of carboxylic acids which have up to 20 carbon atoms, vinyl halides, nonaromatic hydrocarbons having 4 to 8 carbon atoms and 1 or 2 double bonds, unsaturated nitriles, and mixtures thereof. Particular preference is given to polymers consisting to the extent of more than 60% by weight of $C_1$–$C_{10}$-alkyl (meth)acrylates or styrene, or mixtures thereof.

The polymers (A) additionally comprise hydroxy-functional monomers in accordance with the above hydroxyl content and also, if desired, other monomers, for example ethylenically unsaturated acids, especially carboxylic acids, acid anhydrides or acid amides.

Examples of other polymers (A) are polyesterols as obtainable by condensing polycarboxylic acids, especially dicarboxylic acids, with polyols, especially diols.

Other suitable polymers (A) are polyetherols prepared by adding ethylene oxide, propylene oxide or butylene oxide onto H-active components. Polycondensation products of butanediol are also suitable.

The polymers (A) can of course be compounds with primary or secondary amino groups.

Examples which may be mentioned are so-called Jeffamines, ie. amino-terminated polyetherols, or oxazolidines.

Apart from the abovementioned A and B components, the coating compositions can also comprise other polyisocyanates and compounds having polyisocyanate-reactive groups, such compounds customarily being present in two-component coating compositions. Particularly suitable examples of such compounds are the isocyanates used to prepare the compounds of the formula I.

B components for two-component polyurethane coating compositions generally contain 0.2–99.9 mol % of isocyanate groups in the form of the compound of the formula I 0.1–99.8 mol % of isocyanate groups in the form of a compound of the formula II and 0–58.2 mol % of isocyanate groups in the form of a compound of the formula III.

Preferred two-component polyurethane coating compositions comprise, as A component, a polymer (A) having at least 2 isocyanate-reactive groups, preferably alcoholic hydroxyl groups, the molar ratio of the sum formed from the units X, Y, U and V in the compounds of the formulae I and III and the isocyanate-reactive groups of polymer (A) to the sum of the isocyanate groups in the compounds of the formulae I, II and III being from 0.6:1 to 1.4:1, preferably from 0.7:1 to 1.3:1.

Components B which are suitable for use in two-component polyurethane coating compositions are obtained directly if the compounds IV are reacted with the compounds V in a molar ratio of from 1:50 to 1:1.5 until almost all of the isocyanate-reactive groups $R^{IV}$ have been consumed by reaction, and then the unreacted portion of the compounds V is removed from the reaction mixture.

Mixtures which can be employed as one-component polyurethane coating compositions customarily contain 0.2–100 mol %, preferably 0.2–80 mol %, of isocyanate groups in the form of the compound of the formula I 0–58.2 mol %, preferably 10–49.9 mol %, of isocyanate groups in the form of a compound of the formula II and 0–58.2 mol %, preferably 10–49.9 mol %, of isocyanate groups in the form of a compound of the formula III.

It is advantageous to employ those coating compositions in which there are 0.1–10 mol, preferably 0.2–5 mol, of a compound of the formula II per mole of a compound of the formula I, and 0.6–1.4 mol, preferably 0.9–1.1 mol, of a compound of the formula III per mole of NCO groups in the compound of the formula II.

Preferred mixtures are those whose real content of isocyanate groups (NCO groups) is from 1 to 40% by weight, particularly preferably from 5 to 25% by weight (taking the molecular weight of the NCO groups to be 42) and with a theoretical NCO content of from −6 to +6% by weight, particularly preferably from −3 to +3% by weight.

The real NCO content in percent is obtained by measuring the molar quantity of NCO groups per unit weight, which can be found, for example, by generally known titration methods, and multiplying this value by 100 and 42 (molecular weight of -NCO). A customary titration method is described in DIN 53185.

The theoretical NCO content is obtained by calculation, by subtracting the molar quantity of NCO groups per unit weight which corresponds to the molar quantity of units X, Y, U and V per unit weight from the measured molar quantity of the NCO groups per unit weight, and multiplying the result by 4200.

The theoretical NCO content, in percent, is therefore the NCO content which would have resulted had the protected, NCO-reactive groups (units X, Y, U and V) reacted quantitatively with the NCO groups, and for the compounds I is equal to 0.

One-component systems of this kind have virtually unlimited storage lives and only crosslink in the presence of water, for example in the form of atmospheric moisture, since by means of the water the protected units X, Y, U and V are deprotected, ie. converted into isocyanate-reactive groups. Through the choice of the stoichiometric ratio, as defined, of the units X, Y, U and V to isocyanate groups it can be made certain that the compounds form a high molecular weight network, which is vital if the coatings are to attain a high level of technical performance.

The polyisocyanates II can also be replaced in whole or in part by other compounds which react with the reactive component(s). Examples of suitable such compounds are polyepoxides, those containing acid anhydride groups or N-methylol groups, or those containing etherified N-methylol groups, examples being urea resins or melamine resins, which are able to react with the deblocked groups X, Y, U and V of the compounds I and III.

The novel coating compositions can additionally contain organic solvents, for example xylene, butyl acetate, methyl isobutyl ketone, methoxypropyl acetate and N-methylpyrrolidone. Using solvents, the low viscosity of the coating composition, as desired for processing, ie. for application to the substrates, is established. Owing to the compounds I, moreover, substantially less solvent is required; in other words, the relatively low viscosity desired is reached at higher solids contents.

The coating compositions can of course comprise other additives which are customary in coating technology, for example pigments, fillers, leveling agents, etc.

They can also obtain catalysts for urethane formation, for example dibutyltin dilaurate.

The two-component polyurethane coating compositions can be prepared in a known manner. Commonly, the A component and the B component are mixed before the coating compositions are applied to a substrate. The desired viscosity can be established by means of solvent.

The one-component polyurethane coating compositions can be prepared at any point in time prior to their application, since crosslinking is unable to take place spontaneously owing to the fact that the isocyanate-reactive amine, thiol and/or hydroxyl groups are present in protected form, ie. as groups X, Y and, if appropriate, U and V.

Crosslinking takes place after application, when the coating compositions come into contact with water or atmospheric moisture.

Under the influence of water, the blocked, isocyanate-reactive groups in the compounds I and III are liberated. Thereafter, the reaction of the deblocked groups of the formulae I and III with the polyisocyanates takes place at room temperature or at elevated temperature in a known manner.

Both the one- and two-component coating compositions can be applied to substrates in a customary manner, by spraying, flow coating, rolling, brushing, knife coating, etc.

The coating compositions are particularly suitable for workpieces with surfaces of metal, plastic, wood, timber materials, etc.

The coatings obtained have very good mechanical properties, in particular high hardness, flexibility and chemical resistance.

The novel compounds of the formula I have the particular advantage that they can be used to produce high-quality one- and two-component polyurethane coating compositions of particularly low viscosity.

The mixtures of compounds I and the mixtures of the compounds I, II and III are also suitable for use as reactive diluents in two-component polyurethane systems, since they are able to participate in the crosslinking reaction while having virtually no effect on the stoichiometric ratios of the NCO groups to the NCO-reactive groups.

EXAMPLES

Starting compounds of the formula IV

IV.1 2,2-Dimethyl-4-hydroxymethyl-1,3-dioxolane (isopropylideneglycerol)

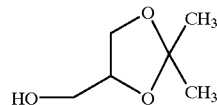

IV.2 4-Aminomethyl-2,2-dimethyl-1,3-dioxolane

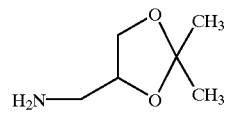

known from F. S. Gibson, M. S. Park and H. Rapoport, J. Org. Chem. 1994, 59, 7503–7507

IV.3 Reaction product of 3 mol of ethylene oxide and compound IV.1

To prepare IV.3, 1060 g (8 mol) of isopropylideneglycerol (IV.1) were charged to a 5 l reactor suitable for preparing polyetherols, 4 g of potassium tert-butylate were added, and the mixture was heated to 110° C. At this temperature, 24 mol of ethylene oxide were added. The reaction was continued until the pressure remained constant.

Reduced pressure was then applied for 30 minutes. After removal of monomer, the reactor was blanketed with nitrogen and cooled to 50° C. and the product was discharged. To remove the alkali, 3% by weight of a Mg silicate (Ambusol, cation exchanger) was added and the mixture was heated at 100° C. for 2 h. The silicate was filtered off and the final product was stabilized with 0.15% by weight of 2,6-di-tert-butyl-p-cresol (Kerobit TBK).

OH number=216

V.4 2,2-Dimethyl-5-ethyl-5-hydroxymethyl-1,3-dioxane (Isopropylidene-TMP)

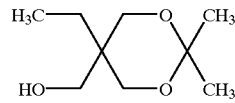

To prepare IV.4, 250 g of trimethylolpropane were refluxed with 750 ml of petroleum ether (boiling range 30–75° C.), 750 ml of acetone and 0.15 g of p-toluenesulfonic acid monohydrate for 24 h. The water of reaction produced was then removed using a water separator. The solution was cooled, 0.5 g of sodium methanolate was added, and the mixture was stirred at room temperature for 1 h. The solution was filtered, the solvent was removed on a rotary evaporator and the residue was distilled under reduced pressure. Yield 78% of theory, boiling point 71–72° C. (0.5 mbar).

IV.5 N-(2-Hydroxyethyl)-2-isopropyloxazolidine

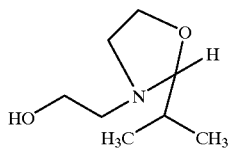

A. B Components for Two-component Coating Compositions comprising compounds I 2000 g of hexamethylene diisocyanate (HDI) were charged to a reactor under a nitrogen blanket, and the appropriate quantity of compound IV.1 to IV.5, according to Table 1, was added. The mixture was heated to 80° C., 0.4 g of the catalyst DABCO TMR 1 (trade name of Air Products for N-(2-hydroxypropyl)trimethylammonium 2-ethylhexanoate) was added, the components were reacted at this temperature and the reaction was terminated, when the mixture had an NCO content of 39–41% by weight, by adding 0.4 g of di-2-ethylhexyl phosphate. In the case of product IV.2, the reaction mixture was heated at 120° C. without catalysis. The reaction mixture was subsequently distilled in order to remove monomeric HDI in a thin-film evaporator at an oil temperature of 165° C. under 2.5 mbar. Subsequently, the content of residual HDI monomer in the end product was below 0.3% by weight.

Comparison Products, Prior Art

Preparation and testing of two-component clearcoats of the novel polyisocyanates The novel products from Table 1 were mixed with a hydroxy-functional vinyl polymer (LUMITOL® H 136, solids content=70%, OHN =136, BASF AG) in accordance with the stoichiometric NCO:OH ratios, and the mixture was catalyzed with 0.1% (based on the solids content) of dibutyltin dilaurate (DBTL, Merck) in order to accelerate curing. Adjustment to an application viscosity of 20 s (DIN 53211 cup 4 mm flow-out nozzle) was made with butyl acetate. The solids contents of the coating material were determined in accordance with DIN V 53 216 part 1, while the VOC values were calculated from mass/volume ratios.

A film drawing frame was used to apply coatings with a wet film thickness of 200 μm to glass plates. The resulting clearcoats were cured for 7 days under standard climatic conditions. The properties of the coatings obtained are summarized in Table 2. For comparison purposes, clearcoats containing BASONAT® HI 100 and BASONAT® P LR 8901 (BASF AG) were tested.

TABLE 2

Testing of clearcoats based on novel polyisocyanates against prior art crosslinking agents

| Clearcoat of product | (Compar. 1) | (Compar. 2) | 4 | 5 | 7 | 9 | 10 | 13 |
|---|---|---|---|---|---|---|---|---|
| Solids content [%] | 45.6 | 50.9 | 53.6 | 58.7 | 61.0 | 53.1 | 64.5 | 52.7 |
| VOC [g/l] | 533 | 479 | 456 | 417 | 393 | 462 | 359 | 465 |

Product 1: BASONAT® HI 100, real NCO content= 22.0%, viscosity at 25° C.=3900 mPas (polyisocyanate, BASF AG)

Product 2: BASONAT®P LR 8901, real NCO content= 20.0%, viscosity at 25° C.=790 mPas (low viscosity polyisocyanate, BASF AG)

Novel Products

TABLE 1

B components

| Product | Starting compound IV | Molar ratio* | NCO content** (% by wt.) | Viscosity at 25° C. (mPas) |
|---|---|---|---|---|
| 3 | IV.1 | 2.5 | 21.1 | 1590 |
| 4 | IV.1 | 5.0 | 20.1 | 810 |
| 5 | IV.1 | 10.0 | 18.4 | 680 |
| 6 | IV.2 | 10.0 | 18.5 | 1310 |
| 7 | IV.3 | 10.0 | 15.9 | 460 |
| 8 | IV.4 | 2.5 | 20.9 | 2150 |
| 9 | IV.4 | 5.0 | 19.6 | 2040 |
| 10 | IV.4 | 10.0 | 17.7 | 2260 |
| 11 | IV.5 | 2.5 | 20.5 | 1540 |
| 12 | IV.5 | 5.0 | 19.1 | 1040 |
| 13 | IV.5 | 10.0 | 17.0 | 1410 |

*Proportion of starting compound of the formula IV relative to HDI [mol %]
**real NCO content The coating materials prepared using the novel polyisocyanate crosslinking agents are not only of outstanding hardness (scratch resistance) and flexibility but also have an enhanced paint solids content relative to the prior art, or a lower solvent content (VOC=volatile organic compounds).

B. One-component polyurethane coating compositions and reactive diluents comprising compounds I Preparation of Products 14 to 17

6 mol of hexamethylene diisocyanate (HDI) were charged to a reactor under a nitrogen blanket and 1.2 mol of the compound IV.1 to IV.5, according to Table 3, were added. The mixture was heated to 80° C., 150 ppm by weight of the catalyst DABCO TMR 1 (trade name of Air Products, N-(2-hydroxypropyl)trimethylammonium 2-ethylhexanoate) were added, the mixture was reacted at this temperature, and the reaction was stopped, at an NCO content of the mixture of 30–32% by weight, by adding 160 ppm by weight of di-2-ethylhexyl phosphate relative to HDI. The reaction mixture was subsequently distilled in order to remove monomeric HDI in a thin-film evaporator at an oil temperature of 165° C. under 2.5 mbar. The content of residual HDI monomer in the end product after this was less than 0.3% by weight.

Preparation of Products 18 to 20

6 mol of IPDI were charged to a reactor under a nitrogen blanket, and 1.2 mol of the component IV were added. The mixture was heated to 70° C., 1200 ppm by weight (based on diisocyanate) of the catalyst DABCO TMR 1 were added, the mixture was reacted at this temperature and the reaction was stopped, at an NCO content of the mixture of 25.5–26.5% by weight, by adding 1300 ppm by weight (based on diisocyanate) of di-2-ethylhexyl phosphate. The reaction mixture was subsequently distilled in order to remove monomeric IPDI in a thin-film evaporator at an oil temperature of 165° C. under 2.5 mbar.

Preparation of Products 21 and 22

6 mol of the diisocyanate were charged to a reactor under a nitrogen blanket, and 1.2 mol of isopropylideneglycerol (IV.1) were added. The mixture was heated to 80° C., 250 ppm by weight (based on diisocyanate) of the catalyst DABCO TMR 1 were added, the mixture was reacted at this temperature, and the reaction was stopped, at an NCO content of the mixture of 24% by weight in the case of BEPDI, or 26% by weight in the case of IPCI, by adding 260 ppm by weight (based on diisocyanate) of di-2-ethylhexyl phosphate. The reaction mixture was subsequently distilled in order to remove monomeric diisocyanate in a thin-film evaporator at an oil temperature of 165° C. under 2.5 mbar.

TABLE 3

| Product No. | Isocyanate | Starting compound IV | NCO theoretical [% by wt.] | NCO real [% by wt.] | Visc. [mPas] |
|---|---|---|---|---|---|
| 14 | HDI | IV.1 | −1.7 | 16.2 | 490 (25° C.) |
| 15 | HDI | IV.3 | −0.3 | 13.8 | 510 (25° C.) |
| 16 | HDI | IV.4 | −1.3 | 15.2 | 2310 (25° C.) |
| 17 | HDI | IV.5 | −1.6 | 15.4 | 1220 (25° C.) |
| 18 | IPDI | IV.1 | −1.2 | 13.4 | 1470* (50° C.) |
| 19 | IPDI | IV.4 | +0.1 | 13.7 | 2950* (50° C.) |
| 20 | IPDI | IV.5 | −1.8 | 12.1 | 3040* (50° C.) |
| 21 | IPCI | IV.1 | 0.0 | 15.4 | 26240 (25° C.) |
| 22 | BEPDI | IV.1 | −1.8 | 12.0 | 19300 (25° C.) |

* = 90% in butyl acetate
HDI = Hexamethylene diisocyanate
IPDI = Isophorone diisocyanate
IPCI = 2-Isocyanatopropylcyclohexyl isocyanate
BEPDI = 2-Butyl-2-ethylpentamethylene diisocyanate Preparation and Testing of One-component Coating Compositions The novel products from Table 3 were mixed with Basonat® HI 100 (in the case of negative theoretical NCO contents, in accordance with the stoichiometry), and 0.1% of dibutyltin dilaurate (DBTL, Merck) was added in order to accelerate curing. Adjustment to an application viscosity of 20 s (DIN 53 211 cup 4 mm flow nozzle) was made with butyl acetate. The solids contents of the coatings were determined in accordance with DIN V 53 216 part 1, while the VOC values were calculated from mass/volume ratios.

The solids contents of paints are summarized in Table 4. For comparison purposes, a clearcoat based on Lumitol® H 136 (hydroxyacrylate resin, 70% in butyl acetate, OHN=135, BASF AG), crosslinked with BASONAT® HI 100 (polyisocyanate, 100%, real NCO content=22%, BASF AG) was tested.

TABLE 4

| Clearcoat from isocyanate No. | Comparison | 14 | 15 | 16 | 17 | 18 | 20 | 21 | 22 |
|---|---|---|---|---|---|---|---|---|---|
| Solids content [%] | 45.6 | 81.2 | 80.0 | 77.4 | 77.0 | 69.9 | 69.3 | 76.6 | 75.3 |
| VOC [g/l] | 533 | 201 | 213 | 238 | 240 | 308 | 309 | 249 | 251 |

The coating materials prepared with the novel isocyanate crosslinking agents are not only of outstanding hardness (scratch resistance) but also have a solids content which is markedly improved relative to the prior art, or a lower solvent content (VOC=volatile organic compounds).

Preparation and Testing of Mixtues as Reactive Diluents

Isocyanate No. 14 was mixed with the coating material of the comparison example from Table 4 in various proportions, and the mixture was catalyzed with 0.1% of dibutyltin dilaurate (DBTL, Merck) in order to accelerate curing. Adjustment to an application viscosity of 20 s (DIN 53 211 cup 4 mm flow nozzle) was made with butyl acetate. The coatings' solids contents were determined in accordance with DIN V 53 216 part 1, while the VOC values were calculated from mass/volume ratios. A film-drawing frame was used to apply coatings with a wet film thickness of 150 μm to glass plates. The resulting clearcoats were cured for 7 days under standard climatic conditions. The resulting coatings properties are summarized in Table 5.

TABLE 5

| Mixing ratio* | | | | | |
|---|---|---|---|---|---|
| Isocynate No. 14 | 0 | 50 | 70 | 85 | 100 |
| Standard coating material | 100 | 50 | 30 | 15 | 0 |
| Mixing ratio** | | | | | |
| Polyisocyanate No.1 | 0 | 56.4 | 75.1 | 88.0 | 100 |
| Standard coating material | 100 | 43.6 | 24.9 | 12.0 | 0 |
| Erichsen indentation [mm] | 8.9 | 9.9 | 10 | 10 | 10 |
| Adhesion/cross-hatch | 0.5 | 0 | 0 | 0 | 0 |
| Scratch resistance | 0 | 0 | 0 | 0 | 0 |
| Solids content [%] | 45.6 | 62.4 | 69.5 | 75.5 | 81.2 |
| VOC [g/l] | 533 | 382 | 316 | 259 | 201 |

*the figure given is the weight ratio
**the figure given is the weight ratio relative to the respective solids content of the components

We claim:

1. An isocyanato compound with capped, isocyanate-reactive groups, of the formula I

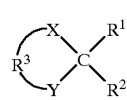

I where $R^1$ and $R^2$ are hydrogen, $C_1$–$C_{10}$-alkyl, $C_6$–$C_{10}$-aryl or $C_7$–$C_{10}$-aralkyl or together form $C_3$–$C_{10}$-alkanediyl, X and Y are —O—, —S— or

where $R^4$ is hydrogen, $C_1$–$C_{20}$-alkyl which is uninterrupted or interrupted by oxygen atoms in ether function, or is $C_6$–$C_{10}$-aryl or $C_7$–$C_{10}$-aralkyl, $R^3$ is $C_1$–$C_{10}$-alkanediyl which together with —X—$CR^1R^2$—Y— forms a 4–7-membered ring, in which either one hydrogen in $R^3$ or the radical $R^4$ in

is replaced by an allophanate group $R^{Ia}$

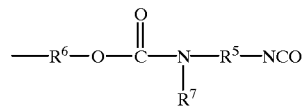

in which $R^5$ is a divalent aliphatic, alicyclic, araliphatic or aromatic $C_2$–$C_{20}$ hydrocarbon unit, $R^6$ is a single bond or a divalent aliphatic, alicyclic, araliphatic or aromatic $C_1$–$C_{20}$ hydrocarbon unit or a mono- or poly($C_2$–$C_4$-alkylene oxide) unit, and $R^7$ is a carbamoyl radical

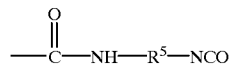

or a biuret group $R^{Ib}$

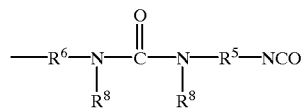

in which one $R^8$ is hydrogen and the other is as defined for $R^7$ or a biuret group $R^{Ic}$

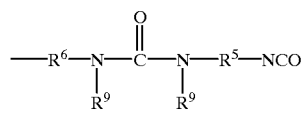

in which one $R^9$ is as defined for $R^7$ and the other is as defined for $R^1$ or a thioallophanate group $R^{Id}$

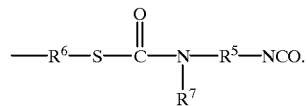

2. A mixture comprising a) 0.2–100 mol % of isocyanate groups in the form of the compound of the general formula I according to claim 1 b) 0–99.8 mol % of isocyanate groups in the form of a customary isocyanate having on average at least 2 isocyanate groups (compound II)

c) 0–58.2 mol % of isocyanate groups in the form of a compound of the formula III

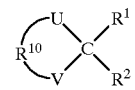

where $R^1$ and $R^2$ are as defined for formula I,

U and V are —O—, —S— or

where $R^{11}$ is hydrogen, $C_1$–$C_{10}$-alkyl which is uninterrupted or interrupted by oxygen atoms in ether function, or is $C_6$–$C_{10}$-aryl or $C_7$–$C_{10}$-aralkyl, and $R^{10}$ is $C_1$–$C_{10}$-alkanediyl which together with —U—$CR^1R^2$—V— forms a 4–7-membered ring, in which either one hydrogen of $R^{10}$ or the radical $R^{11}$ in

is substituted by a urethane group $R^{IIIa}$

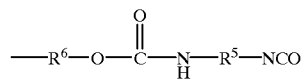

or a urea group $R^{IIIb}$

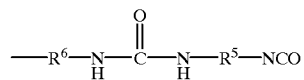

or a urea group $R^{IIIc}$

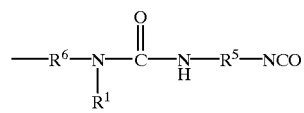

or a thiourethane group $R^{IIId}$ $$—R^6—S—\overset{\overset{O}{\|}}{C}—\underset{H}{N}—R^5—NCO$$

in which $R^1$, $R^5$ and $R^6$ are as defined for formula I.

3. A mixture as claimed in claim 2, where the compound II is of the general formula (IIa)

IIa

[structure of isocyanurate ring with three $R^5$-NCO substituents]

or an oligomeric form deriving therefrom.

4. A process for preparing a mixture as claimed in claim 3, which comprises reacting a compound of the formula IV

IV

[structure showing cyclic compound with D, E, $R^1$, $R^2$, $R^{12}$]

where
$R^1$ and $R^2$ are as defined in formula I,

I

[structure showing cyclic compound with X, Y, $R^1$, $R^2$, $R^3$]

D and E are —O—, —S— or $$—NR^{13},$$

where $R^{13}$ is hydrogen, $C_1$–$C_{10}$-alkyl which is uninterrupted or interrupted by oxygen atoms in ether function, or is $C_6$–$C_{10}$-aryl or $C_7$–$C_{10}$-aralkyl, and $R^{12}$ is $C_1$–$C_{10}$-alkanediyl which together with D-$CR^1R^2$-E forms a 4–7-membered ring, in which either one hydrogen in $R^{12}$ or the radical $R^{13}$ in $$—NR^{13}$$

is substituted by a radical $R^{IVa}$

—$R^6$—OH, a radical $R^{IVb}$

—$R^6$—$NH_2$, or a radical $R^{IVc}$

—$R^6$—NH
          |
          $R^7$ or a radical $R^{IVd}$

—$R^6$—SH with a compound of the formula V

OCN—$R^5$—NCO at from 20 to 140° C. with a molar ratio of the compound of formula IV to the compound of formula V of from 1:1.5 to 1:20.

5. A process as claimed in claim 4, wherein the unreacted portions of the compound of the formula V are separated off after the end of the reaction down to a content of less than 1% by weight.

6. A B component for two-component polyurethane coating compositions, comprising the mixture according to claim 2, wherein 0.2–99.9 mol % of isocyanate groups in the form of the compound of the formula I 0.1–99.8 mol % of isocyanate groups in the form of a compound of compound II and 0–58.2 mol % of isocyanate groups in the form of a compound of the formula III.

7. A two-component polyurethane coating composition comprising a B component as claimed in claim 6 and an A component having at least 2 NCO-reactive groups with the proviso that the molar ratio of the sum formed from the units X, Y, U and V in the compounds of the formulae I and III and the NCO-reactive groups of the A component to the sum of the isocyanate groups in the compounds of the formulae I, II and III is from 0.6:1 to 1.4:1.

8. A one-component polyurethane coating composition comprising the mixture according to claim 2, wherein;

0.2–100 mol % of isocyanate groups in the form of a compound of the formula I

0–58.2 mol % of isocyanate groups in the form of a compound of compound II and

0–58.2 mol % of isocyanate groups in the form of a compound of the formula III.

9. A coating method which comprises coating an article with a two-component polyurethane coating composition as claimed in claim 6.

10. A coating method which comprises coating an article with a one-component polyurethane coating composition as claimed in claim 8.

11. A method of coating, comprising coating an article with a two-component polyurethane coating composition as claimed in claim 7.

* * * * *